(12) United States Patent
Milne

(10) Patent No.: US 9,603,681 B2
(45) Date of Patent: Mar. 28, 2017

(54) SYSTEMS AND METHODS FOR ATTACHMENT OF DENTAL PROSTHESES

(71) Applicant: Robert Milne, Sherwood, OR (US)

(72) Inventor: Robert Milne, Sherwood, OR (US)

( * ) Notice: Subject to any disclaimer, the term of this patent is extended or adjusted under 35 U.S.C. 154(b) by 235 days.

(21) Appl. No.: 14/551,351

(22) Filed: Nov. 24, 2014

(65) Prior Publication Data

US 2016/0143713 A1     May 26, 2016

(51) Int. Cl.
*A61C 8/00* (2006.01)
*A61C 3/16* (2006.01)

(52) U.S. Cl.
CPC .............. *A61C 8/0081* (2013.01); *A61C 3/16* (2013.01); *A61C 8/0062* (2013.01); *A61C 8/0068* (2013.01)

(58) Field of Classification Search
CPC ........ A61C 13/235; A61C 8/0081; A61C 8/00
See application file for complete search history.

(56) References Cited

U.S. PATENT DOCUMENTS 6,171,107 B1 *   1/2001   Milne .................. A61C 8/0081
                                                              156/272.4

* cited by examiner

*Primary Examiner* — Jason-Dennis Stewart
(74) *Attorney, Agent, or Firm* — Mohr Intellectual Property Law Solutions, PC

(57) ABSTRACT

Dental implant systems for releasable attachment of dental prostheses are shown and described. Each of the dental implant systems includes an implant body, a prosthesis body, and an abutment body with a locking device. The locking device includes a magnetically attractable member having a first end coupled to a spring and a second end. The magnetically attractable member is moveable between a locked position and an unlocked position. The dental implant system further includes a void configured to receive the second end, the magnetically attractable member being at least partially disposed within the void in the locked position, the magnetically attractable member being free of the void in the unlocked position.

12 Claims, 7 Drawing Sheets

SYSTEMS AND METHODS FOR ATTACHMENT OF DENTAL PROSTHESES

BACKGROUND

The present disclosure relates generally to devices and methods for attachment of dental prostheses. In particular, methods and devices for releasable mechanical attachment of dental prostheses are described.

Dental implants are anchoring devices which are placed into the jaw bones. The bone does not reject these implants which for the most part are made of Titanium, a relatively inert metal. The implants become integrated into the bone so that they function as solid anchors onto which various types of dental prosthetic devices can be attached thus replacing missing single teeth or more extensive sections of teeth up to and including complete replacement of all of a patient's dentition. Most of the dental prostheses techniques involving crown and bridge replacements use a cementation of the crown to an abutment which is affixed to the dental implant usually by a retention screw.

These known dental prostheses attachment techniques and methods are not entirely satisfactory for the range or applications in which they are employed. For example, the retention screws are inside of the abutment and the crowns are cemented over the abutment. Often the cement margin (i.e., the crown/abutment interface), is located below the level of the gums (i.e., gingiva). It is well-documented that some of this cement can remain below the gum level, resulting in an inflammatory reaction which can result in loss of bone and in extreme cases even the loss of the implant.

In addition, conventional dental prostheses attachment techniques and methods are not easily removable if there is need for repair and/or adjustments to a dental prosthesis, and/or treatment of the supporting bone or gingiva of that prosthesis. If the prosthesis has been cemented with permanent cement, removal is impossible without damaging the prosthesis. Even if temporary cement has peen used, removal is often very difficult and time consuming and often results in damage to the prosthesis.

Thus, there exists a need for dental prostheses attachment methods and devices that improve upon and advance the design of known dental prostheses attachment techniques. Examples of new and useful dental prostheses attachment methods and devices relevant to the needs existing in the field are discussed below.

Disclosure addressing one or more of the identified existing needs is provided in the detailed description below. Examples of references relevant to dental prostheses attachment methods and devices include U.S. Patent References: U.S. Pat. No. 3,747,215, U.S. Pat. No. 4,431,416, U.S. Pat. No. 4,488,874, U.S. Pat. No. 4,626,213, U.S. Pat. No. 4,880,383, U.S. Pat. No. 4,907,969, U.S. Pat. No. 5,002,489, U.S. Pat. No. 5,015,186, U.S. Pat. No. 6,030,219, U.S. Pat. No. 6,299,447, U.S. Pat. No. 702,857, U.S. Pat. No. 7,524, 188, U.S. Pat. No. 8,475,167, patent publication 2013/0101960. The complete disclosures of the above patents and patent applications are herein incorporated by reference for all purposes.

SUMMARY

The present disclosure is directed to dental implant systems for releasable attachment of dental prostheses. Each of the dental implant systems includes an implant body, a prosthesis body, and an abutment body with a locking device. The locking device includes a magnetically attractable member having a first end coupled to a spring and a second end. The magnetically attractable member is moveable between a locked position and an unlocked position. The dental implant system further includes a void configured to receive the second end, the magnetically attractable member being at least partially disposed within the void in the locked position, the magnetically attractable member being free of the void in the unlocked position.

DETAILED DESCRIPTION

Figure 1:
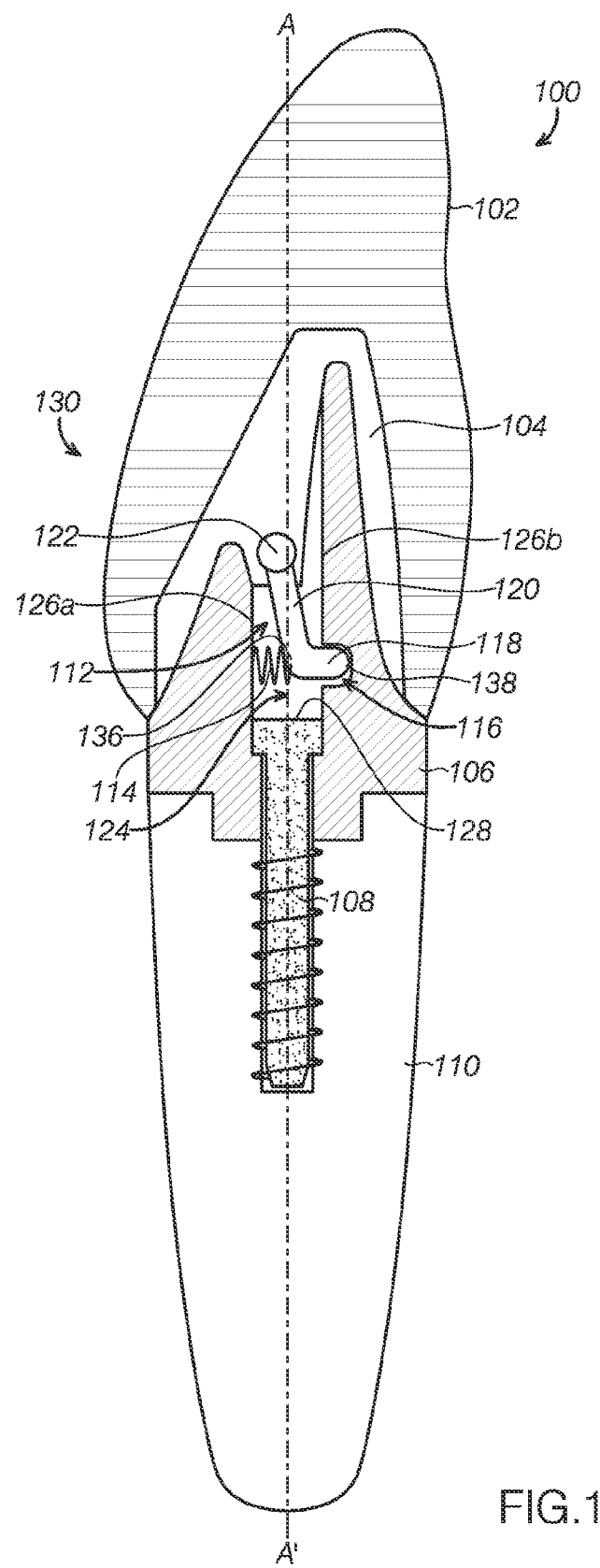
FIG. 1 is a cross-sectional of a first example of a dental prosthesis attachment mechanism in a locked configuration.

The disclosed dental prostheses attachment methods and devices will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity; each and every contemplated variation is not individually described in the following detailed description.

Throughout the following detailed description, examples of various dental prostheses attachment methods and devices are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

With reference to FIGS. 1-7, first, second, and third examples of dental prostheses attachment systems, attachment systems 100, 200, and 300, respectively, will now be described. Each of attachment systems 100, 200, and 300 includes a prosthesis body (102, 202, 302) an abutment main body (106, 206, 306), an implant body (110, 210, 310), and a locking mechanism (112, 212, 312). Locking mechanisms 112, 212, and 312 each function to mechanically attach the prosthesis body to the abutment body and/or the implant body. Additionally or alternatively, locking mechanisms 112, 212, and 312 can be used to releasably attach the prosthesis to the abutment, so that the prosthesis can be selectively attached and removed from the abutment main body and/or the implant body.

Attachment systems 100, 200, and 300 address many of the shortcomings existing with conventional dental prostheses attachment systems. For example, the presently described attachment systems can be attached without the use of cement, thereby reducing the risk of an inflammatory reaction, bone loss, and/or loss of the implant. In another example, the presently described attachment systems are releasable so that a dental prosthesis can be removed if there is need for repair and/or adjustments to the dental prosthesis, or if there is need for treatment of the underlying supporting bone or gingiva of the prosthesis. Further, in even another example, dental prostheses can be quickly attached and/or released, requiring less time than conventional dental prostheses attachment and/or removal techniques.

Figure 2:
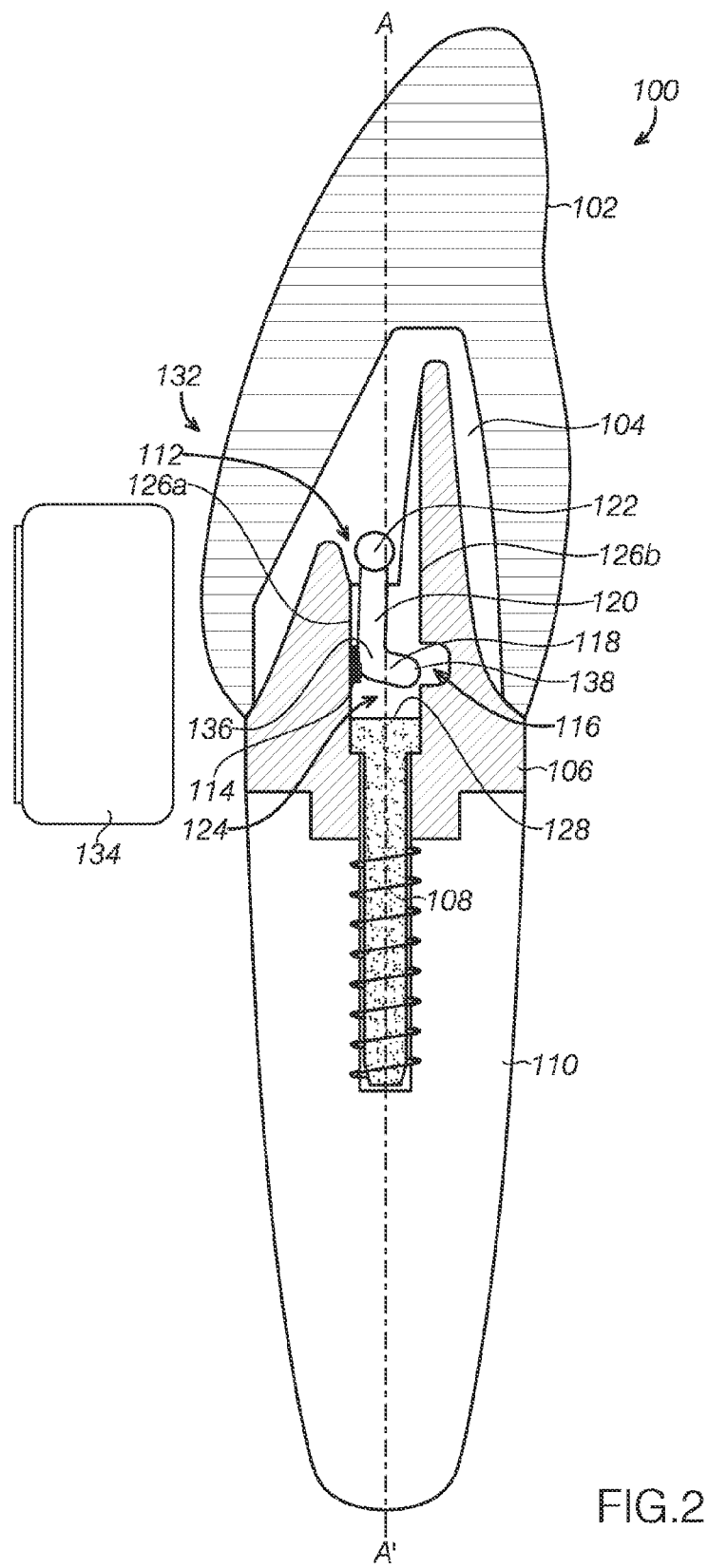
FIG. 2 is a cross-sectional view of the first example dental prosthesis attachment mechanism of FIG. 1 in an unlocked configuration.

As can be seen in FIGS. 1 and 2, attachment system 100 includes prosthesis body 102, an abutment cover 104, abutment main body 106, an abutment screw 108, implant body 110, and locking mechanism 112. In the present example, abutment cover 104 and abutment main body 106, in combination, form an abutment body. Prosthesis body 102 is permanently attached to underlying abutment cover 104 via direct bonding, cement, and/or adhesive.

Further, abutment main body 106 is attached to implant body 110 via abutment screw 108 (i.e., the abutment screw is threadably attached to the implant body). In alternate examples, the prosthesis body can be attached to the abutment cover via different mechanism (e.g., the abutment cover can be an integral cast part of the prosthetic body, such as a metallic prosthetic body cast to a metallic abutment cover) and/or the abutment main body can be attached to the implant body via a different mechanism (e.g., the abutment main body can be swedged to the implant body such as a Morris Taper, being cemented to the implant body, etc.).

In the example of attachment system 100, locking mechanism 112 is configured to attach abutment cover 104 to abutment main body 106 and to release abutment cover 104 from abutment main body 106. Locking mechanism 112 includes a spring member 114, a void 116, and a moveable member 118. Locking mechanism 112 further includes an elongate member 120 (i.e., a hinge member) that is hingedly attached to abutment cover 104 via a hinge 122. One end of elongate member 120 is attached to hinge 122 and a second opposing end is attached to or continuous with moveable member 118. Moveable member 118 is generally horizontally arranged relative to a vertical axis A-A' of prosthesis body 102 and implant body 110, while elongate member 120 is generally aligned with vertical axis A-A'. Locking mechanism 112 is disposed within a space 124 between abutment cover 104, internal abutment main body walls 126 (126a and 126b), and a top surface 128 of abutment screw 108.

As depicted in FIGS. 1 and 2, locking mechanism 112 is moveable between a locked position 130 (shown in FIG. 1) and an unlocked position 132 (shown in FIG. 2). In locked position 130, spring member 114 is extended and exerts a biasing force on a first end 136 moveable member 118. Accordingly, moveable member 118 is pivoted (i.e., elongate member 120 is pivoted around hinge 122) so that at least a second end 138 of the moveable member is extended into and retained in void 116. In other words, the moveable member is at least partially disposed in the void in the locked position. Further, in locked position 130, moveable member 118 is interposed between prosthesis body 102/abutment cover 104 and abutment main body 106. Accordingly, in the locked position, the moveable member resists vertical movement of the prosthesis body (i.e., movement along vertical axis A-A') and resists separation of the prosthesis body from the abutment main body.

In unlocked position 132, a magnetically attractable dental prosthesis removal device 134 is disposed proximal to first end 136 of moveable member 118. Removal device 134 has a magnetic interaction with moveable member 118 that moves second end 138 of moveable member 118 out of void 116 and compresses spring member 114 between first end 136 and wall 126a. In other words, the moveable member is substantially free of the void in the unlocked position. Thus, moveable member 118 is removed from its interposed position between prosthesis body 102/abutment cover 104 and abutment main body 106 by application of the magnetic force (i.e., the magnetic interaction). Accordingly, in the unlocked position, the prosthesis body is capable of vertical movement (i.e., movement along vertical axis A-A') and capable of separation of the prosthesis body from the abutment main body.

In the present example, both of removal device 134 and moveable member 118 are magnetically attractable members. In one specific example, removal device 134 is a magnet (e.g., an electromagnetic device, a rare earth magnet, etc.) and moveable member 118 is comprised of one or more magnetically attractable materials (e.g., iron, steel, nickel, cobalt, gadolinium, etc.). In alternate examples, removal device 134 can be comprised of one or more magnetically attractable materials and moveable member 118 can be a magnet. Further, in the present example, spring member 114 is a coil spring. In alternate examples, the spring member can have a different configuration that is capable of extension and compression (e.g., volute spring, torsion spring, etc.).

It will be appreciated that locking mechanism 112 can be selectively moved between locked position 130 and unlocked position 132 for selective attachment and detachment of prosthesis body 102. In one example for attachment of the prosthesis body, prosthesis body 102 is moved downward along vertical axis A-A' and second end 138 of moveable member 118 is slid over wall 126b. In this example, spring 114 is in a partially compressed state until moveable member 118 reaches void 116. Spring 114 then extends and second end 138 of moveable member 118 is extended into void 116.

In a second example for attachment of the prosthesis body, magnetically attractable removal device 134 is held proximal to first end 136 of moveable member 118 and spring 114 is moved into a compressed state. Prosthesis body 102 is moved downward along vertical axis A-A' until moveable member 118 is at the level of void 116. Magnetically attractable removal device 134 is then removed and spring 114 is extended so that second end 138 of moveable member 118 is extended into void 116.

In both of the above examples, the prosthesis body can be selectively removed by placing magnetically attractable removal device 134 proximal to first end 136 of moveable member 118 to pivot the moveable member into unlocked position 132 and moving prosthesis body 102 upward along vertical axis A-A'. Accordingly, the dentist or practitioner can selectively move the locking mechanism between the locked and unlocked positions to attach and/or detach the implant/prosthesis complex at any time he/she sees a clinical need to do so. The prosthesis can be attached and detached at will with a process that is less time consuming, less problematic and significantly more user friendly than the standard dental prosthesis attachment systems and methods.

Figure 3:
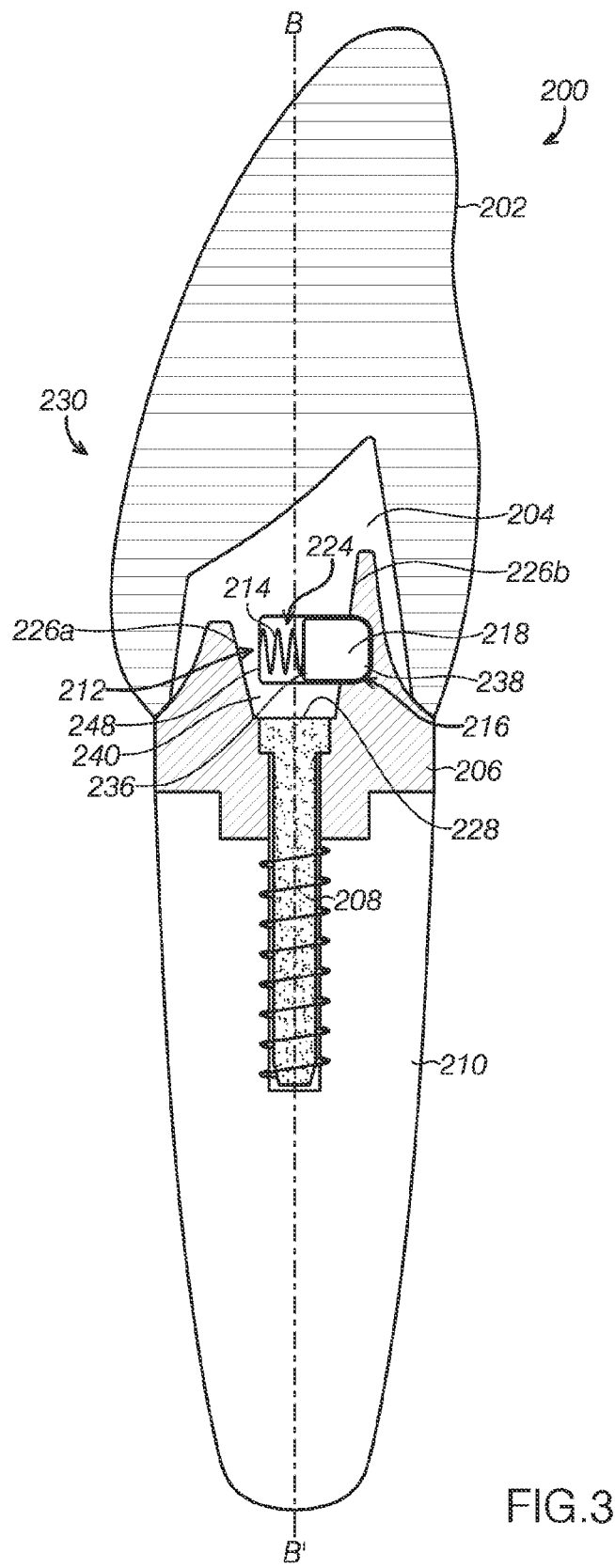
FIG. 3 is a cross-sectional view of a second example of a dental prosthesis attachment mechanism in a locked configuration.
Figure 4:
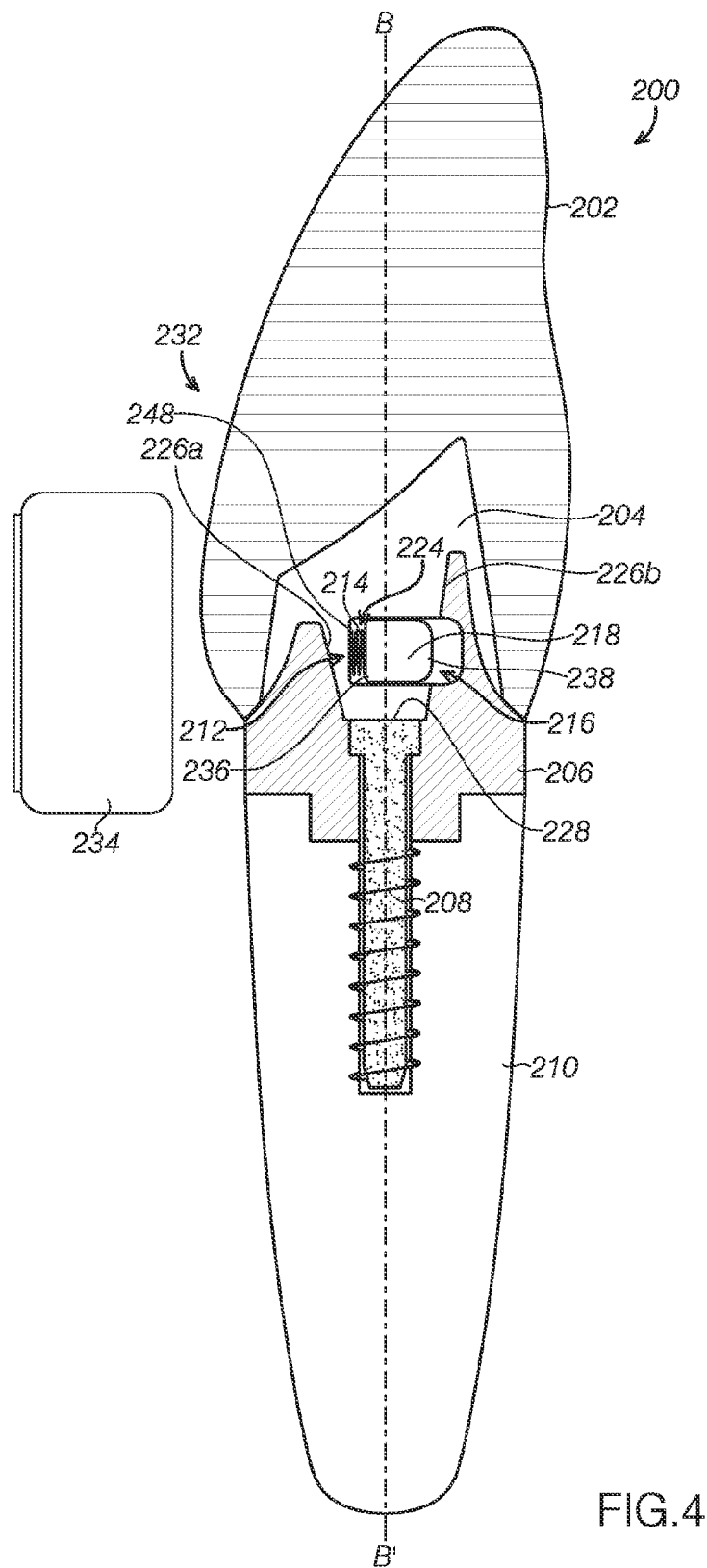
FIG. 4 is a cross-sectional view of the second example dental prosthesis attachment mechanism of FIG. 3 in an unlocked configuration.

Turning attention to FIGS. 3 and 4, a second example of a dental prostheses attachment system, attachment system 200, will now be described. Attachment system 200 includes many similar or identical features to attachment system 100. Thus, for the sake of brevity, each feature of attachment system 200 will not be redundantly explained. Rather, key distinctions between attachment systems 100 and 200 will be described in detail and the reader should reference the discussion above for features substantially similar between the two attachment systems.

As can be seen in FIGS. 3 and 4, attachment system 200 includes prosthesis body 202, an abutment cover 204, abutment main body 206, an abutment screw 208, implant body 210, and locking mechanism 212. In the present example, abutment cover 204 and abutment main body 206, in combination, form an abutment body. Prosthesis body 202 is permanently attached to underlying abutment cover 204 via direct bonding, cement, and/or adhesive.

Further, abutment main body 206 is attached to implant body 210 via abutment screw 208 (i.e., the abutment screw is threadably attached to the implant body). In alternate examples, the prosthesis body can be attached to the abutment cover via a different mechanism (e.g., the abutment cover can be an integral cast part of the prosthetic body, such as a metallic prosthetic body cast to a metallic abutment cover) and/or the abutment main body can be attached to the implant body via a different mechanism (e.g., the abutment main body can be swedged to the implant body such as a Morris Taper, being cemented to the implant body, etc.).

In the example of attachment system 200, locking mechanism 212 is configured to attach abutment cover 204 to abutment main body 206 and to release abutment cover 204 from abutment main body 206. Locking mechanism 212 includes a spring member 214, a void 216, and a moveable member 218. Differently than locking mechanism 112, locking mechanism 212 is generally disposed within a space 224 that is within abutment cover 204. As shown in FIGS. 3 and 4, space 224 is continuous with void 216 and moveable member 218 is slideable within space 224 and void 216. Moveable member 218, space 224, and void 216 are generally horizontally arranged relative to a vertical axis B-B' of prosthesis body 202 and implant body 210. Space 224 is substantially a horizontal channel that is continuous with void 216.

A projection 240 is a central extended portion of abutment cover 204 in which space 224 is disposed. Projection 240 contacts internal abutment main body walls 226 (226a and 226b) and a top surface 228 of abutment screw 208. Projection 240 is generally aligned with vertical axis B-B'.

As depicted in FIGS. 3 and 4, locking mechanism 212 is moveable between a locked position 230 (shown in FIG. 3) and an unlocked position 232 (shown in FIG. 4). In locked position 230, spring member 214 is extended and exerts a biasing force on a first end 236 of moveable member 218. Accordingly, moveable member 218 is horizontally slid into void 216, so that at least a second end 238 of the moveable member is extended into and retained in void 216. In other words, the moveable member is at least partially disposed in the void in the locked position. Further, in locked position 230, moveable member 218 is interposed between prosthesis body 202/abutment cover 204 and abutment main body 206. Accordingly, in the locked position, the moveable member resists vertical movement of the prosthesis body (i.e., movement along vertical axis B-B') and resists separation of the prosthesis body from the abutment main body.

In unlocked position 232, a magnetically attractable dental prosthesis removal device 234 is disposed proximal to first end 236 of moveable member 218. Removal device 234 has a magnetic interaction with moveable member 218 that moves (i.e., slides) second end 238 of moveable member 218 out of void 216 and compresses spring member 214 between first end 236 and an inner side wall 248 of space 224. In other words, the moveable member is substantially free of the void in the unlocked position. Thus, moveable member 218 is removed from its interposed position between prosthesis body 202/abutment cover 204 and abutment main body 106 by application of the magnetic force (i.e., the magnetic interaction). Accordingly, in the unlocked position, the prosthesis body is capable of vertical movement (i.e., movement along vertical axis B-B') and capable of separation of the prosthesis body from the abutment main body.

In the present example, both of removal device 234 and moveable member 218 are magnetically attractable members. In one specific example, removal device 234 is a magnet (e.g., an electromagnetic device, a rare earth magnet, etc.) and moveable member 218 is comprised of one or more magnetically attractable materials (e.g., iron, steel, nickel, cobalt, gadolinium, etc.). In alternate examples, removal device 234 can be comprised of one or more magnetically attractable materials and moveable member 218 can be a magnet. Further, in the present example, spring member 214 is a coil spring. In alternate examples, the spring member can have a different configuration that is capable of extension and compression (e.g., volute spring, torsion spring, etc.).

It will be appreciated that locking mechanism 212 can be selectively moved between locked position 230 and unlocked position 232 for selective attachment and detachment of prosthesis body 202. In one example for attachment of the prosthesis body, prosthesis body 202 is moved downward along vertical axis B-B' and second end 238 of moveable member 218 is slid over wall 226b. In this example, spring 214 is in a partially compressed state until moveable member 218 reaches void 216. Spring 214 then extends and second end 238 of moveable member 218 is extended into void 216.

In a second example for attachment of the prosthesis body, magnetically attractable removal device 234 is held proximal to first end 236 of moveable member 218 and spring 214 is moved into a compressed state. Prosthesis body 202 is moved downward along vertical axis B-B' until moveable member 218 is at the level of void 216. Magnetically attractable removal device 234 is then removed and spring 214 is extended so that second end 238 of moveable member 218 is extended into void 216.

In both of the above examples, the prosthesis body can be selectively removed by placing magnetically attractable removal device 234 proximal to first end 236 of moveable member 218 to pivot the moveable member into unlocked position 232 and moving prosthesis body 202 upward along vertical axis B-B'. Accordingly, the dentist or practitioner can selectively move the locking mechanism between the locked and unlocked positions to attach and/or detach the implant/prosthesis complex at any time he/she sees a clinical need to do so. The prosthesis can be attached and detached at will with a process that is less time consuming, less problematic and significantly more user friendly than the standard dental prosthesis attachment systems and methods.

Figure 5:
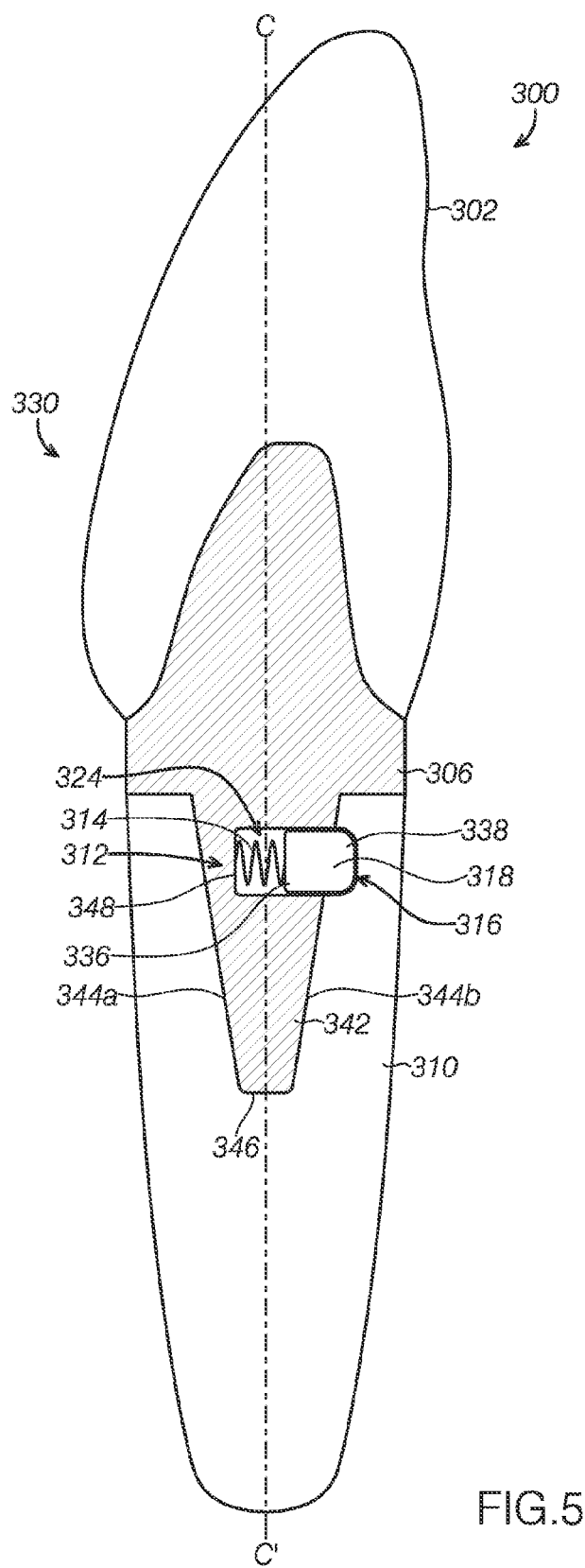
FIG. 5 is a cross-sectional view of third example of a dental prosthesis attachment mechanism in a locked configuration.
Figure 6:
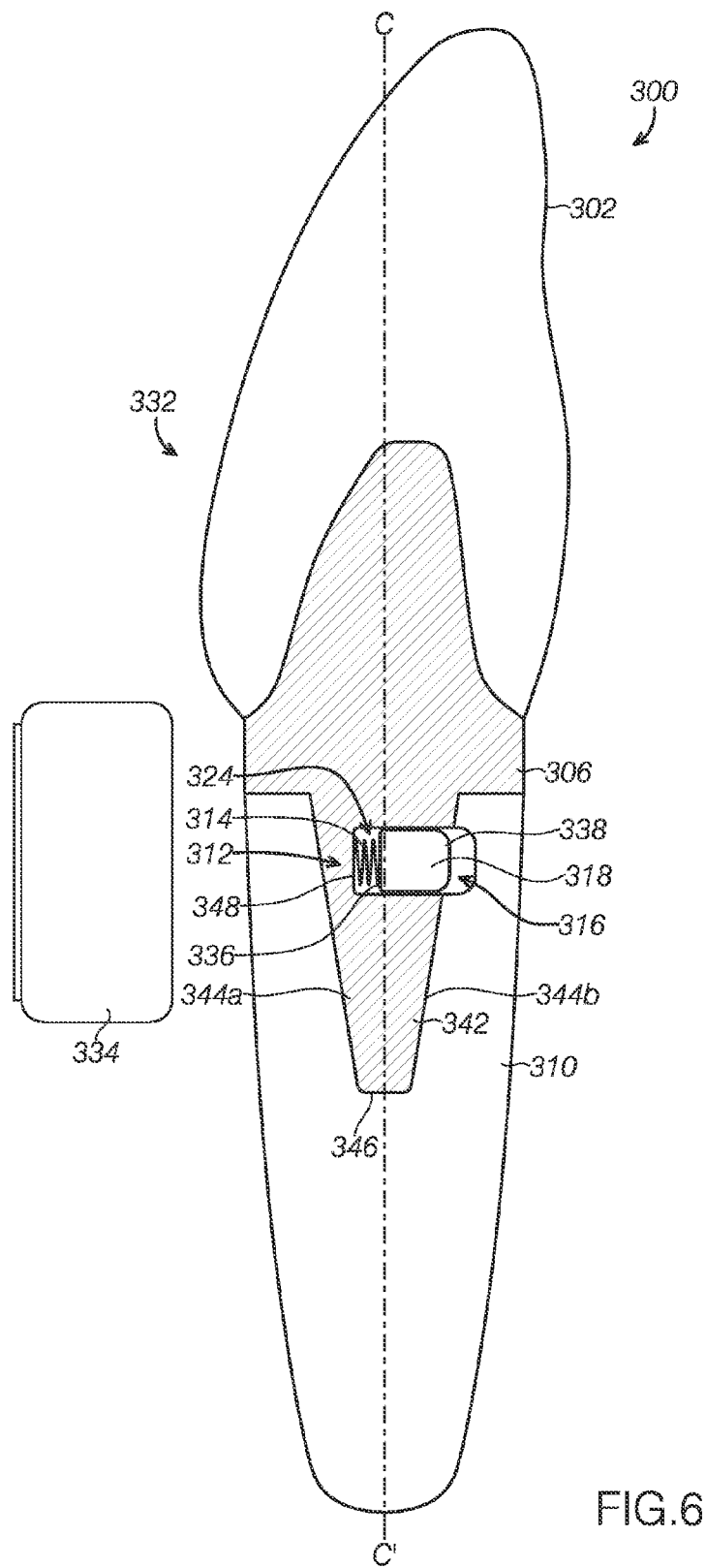
FIG. 6 is a cross-sectional view of the third example dental prosthesis attachment mechanism of FIG. 5 in an unlocked configuration.

Turning attention to FIGS. 5 and 6, third example of a dental prostheses attachment system, attachment system 300, will now be described. Attachment system 300 includes many similar or identical features to attachment systems 100 and 200. Thus, for the sake of brevity, each feature of attachment system 300 will not be redundantly explained. Rather, key distinctions between attachment systems 300 and 100 and 200 will be described in detail and the reader should reference the discussion above for features substantially similar between the three attachment systems.

As can be seen in FIGS. 5 and 6, attachment system 300 includes prosthesis body 302, abutment body 306, implant body 310, and locking mechanism 312. Differently from attachment systems 100 and 200, attachment system 300 excludes an abutment cover and an abutment screw. Further, prosthesis body 302 is permanently attached directly to abutment body 306 via direct bonding, cement, and/or adhesive. In alternate examples, the prosthesis body can be attached to the abutment body via a different mechanism (e.g., direct casting of a metal to which porcelain can be stacked to complete a white tooth type of prosthesis).

Therefore rather than being a mechanism for attachment of the prosthesis body and the abutment cover to the abutment main body, attachment mechanism 300 is a mechanism for attachment of abutment body 302 to implant body 310. More specifically, in the example of attachment system 300, locking mechanism 312 is configured to attach abutment body 306 to implant body 310 and to release abutment body 306 from implant body 310. Locking mechanism 312 includes a spring member 314, a void 316, and a moveable member 318. Differently than locking mechanism 112, locking mechanism 312 is generally disposed within a space 324 that is within abutment body 306. As shown in FIGS. 5 and 6, space 324 is continuous with void 316 and moveable member 318 is slideable within space 324 and void 316. Moveable member 318, space 324, and void 316 are generally horizontally arranged relative to a vertical axis C-C' of prosthesis body 302 and implant body 310. Space 324 is substantially a horizontal channel that is continuous with void 316.

A projection 342 is a central extended portion of abutment body 306 in which space 324 is disposed. Projection 342 contacts internal implant body walls 344 (344a and 344b) and an internal implant body bottom wall 346. Projection 342 is generally aligned with vertical axis C-C'.

As depicted in FIGS. 5 and 6, locking mechanism 312 is moveable between a locked position 330 (shown in FIG. 5) and an unlocked position 332 (shown in FIG. 6). In locked position 330, spring member 314 is extended and exerts a biasing force on a first end 336 of moveable member 318. Accordingly, moveable member 318 is horizontally slid into void 316, so that at least a second end 338 of the moveable member is extended into and retained in void 316. In other words, the moveable member is at least partially disposed in the void in the locked position. Further, in locked position 330, moveable member 318 is interposed between prosthesis body 302/abutment body 306 and implant body 310. Accordingly, in the locked position, the moveable member resists vertical movement of the prosthesis body (i.e., movement along vertical axis C-C') and resists separation of the prosthesis body from the abutment main body.

In unlocked position 332, a magnetically attractable dental prosthesis removal device 334 is disposed proximal to first end 336 of moveable member 318. Removal device 334 has a magnetic interaction with moveable member 318 that moves (i.e., slides) second end 338 of moveable member 318 out of void 316 and compresses spring member 314 between first end 336 and an inner side wall 348 of space 324. In other words, the moveable member is substantially free of the void in the unlocked position. Thus, moveable member 318 is removed from its interposed position between prosthesis body 302/abutment body 306 and implant body 310 by application of the magnetic force (i.e., the magnetic interaction). Accordingly, in the unlocked position, the prosthesis body is capable of vertical movement (i.e., movement along vertical axis C-C') and capable of separation of the prosthesis body from the implant body.

In the present example, both of removal device 334 and moveable member 318 are magnetically attractable members. In one specific example, removal device 334 is a magnet (e.g., an electromagnetic device, a rare earth magnet, etc.) and moveable member 318 is comprised of one or more magnetically attractable materials (e.g., iron, steel, nickel, cobalt, gadolinium, etc.). In alternate examples, removal device 334 can be comprised of one or more magnetically attractable materials and moveable member 318 can be a magnet. Further, in the present example, spring member 314 is a coil spring. In alternate examples, the spring member can have a different configuration that is capable of extension and compression (e.g., volute spring, torsion spring, etc.).

It will be appreciated that locking mechanism 312 can be selectively moved between locked position 330 and unlocked position 332 for selective attachment and detachment of prosthesis body 302. In one example for attachment of the prosthesis body, prosthesis body 302 is moved downward along vertical axis C-C' and second end 338 of moveable member 318 is slid over wall 334b. In this example, spring 314 is in a partially compressed state until moveable member 318 reaches void 316. Spring 314 then extends and second end 338 of moveable member 318 is extended into void 316.

In a second example for attachment of the prosthesis body, magnetically attractable removal device 334 is held proximal to first end 336 of moveable member 318 and spring 314 is moved into a compressed state. Prosthesis body 302 is moved downward along vertical axis C-C' until moveable member 318 is at the level of void 316. Magnetically attractable removal device 334 is then removed and spring 314 is extended so that second end 338 of moveable member 318 is extended into void 316.

In both of the above examples, the prosthesis body can be selectively removed by placing magnetically attractable removal device 334 proximal to first end 336 of moveable member 318 to pivot the moveable member into unlocked position 332 and moving prosthesis body 302 upward along vertical axis C-C'. Accordingly, the dentist or practitioner can selectively move the locking mechanism between the locked and unlocked positions to attach and/or detach the implant/prosthesis complex at any time he/she sees a clinical need to do so. The prosthesis can be attached and detached at will with a process that is less time consuming, less problematic and significantly more user friendly than the standard dental prosthesis attachment systems and methods.

In each of the above example attachment systems, the locking mechanism (e.g., spring activated mechanical lock) prevents the implant complex from being separated in an axial direction, which is defined by a line extending from the apex of the implant body through the implant body and implant abutment and exiting through the coronal tip of the implant prosthesis (i.e., vertical axes A-A', B-B', and C-C'). It will be appreciated that retention of implant prostheses can be primarily derived from the design of the abutments (i.e., precision fit of the prosthesis to the abutment and/or the implant body), which means that the abutment/prosthesis interface can substantially resist lateral forces and can resist axial/vertical displacement forces to a great extent. Because of the precision design of implant components, they are already somewhat resistant to the axial displacement forces and the locking mechanism only need resist the remainder of those axial/vertical forces (e.g., lesser forces normally applied to dental prostheses by mastication within the oral cavity).

This is accomplished in attachment systems 100 and 200 by the spring biasing and/or pressing on the moveable member (i.e., horizontal strut) of the locking mechanism so that the moveable member is inserted and retained between the abutment main body and the abutment cover (i.e., partially retained in the void). More specifically, when the moveable member is partially inserted and retained within the void, a top wall of the moveable member is abutted to a top wall of the void. This prevents movement of the abutment main body and the abutment cover relative to each other.

In attachment system 300, the spring presses and/or biases the moveable member (i.e., horizontal strut) so that the moveable member is inserted and retained between the abutment body and the implant body (i.e., partially retained in the void). More specifically, when the moveable member is partially inserted and retained within the void, a top wall of the moveable member is abutted to a top wall of the void. This prevents relative movement between the abutment body and the implant body.

To disconnect each of the locking mechanisms, a magnetic force (e.g. a magnetic force from an electromagnet, a rare earth magnet, and/or an other magnet known or yet to be discovered) is applied to the implant complex in a direction that counters the force of the spring that presses and/or biases the moveable member of the locking mechanism into the void, and thus the moveable member is pulled out of void toward the magnetic force. In this example, the moveable member is constructed of a ferrous type metal or combination of metals. The moveable member can further include a coating of a material resistant to oxidation (e.g., platinum, gold, titanium oxide, plastic, non-metallic crystals, etc.).

To apply the magnetic force to the implant complex for releasing the locking mechanism (i.e., moving the locking mechanism into the unlocked position), a forceps-like device can be used to simultaneously grasp the implant prosthesis while aligning a magnetic or an electromagnetic device to counter the biasing force of the spring. The forceps-like device can facilitate removal of the prosthesis while the spring lock is held open by the magnetic force. The forceps-like device is one example of a magnetically attractable dental prosthesis removal device.

Figure 7:
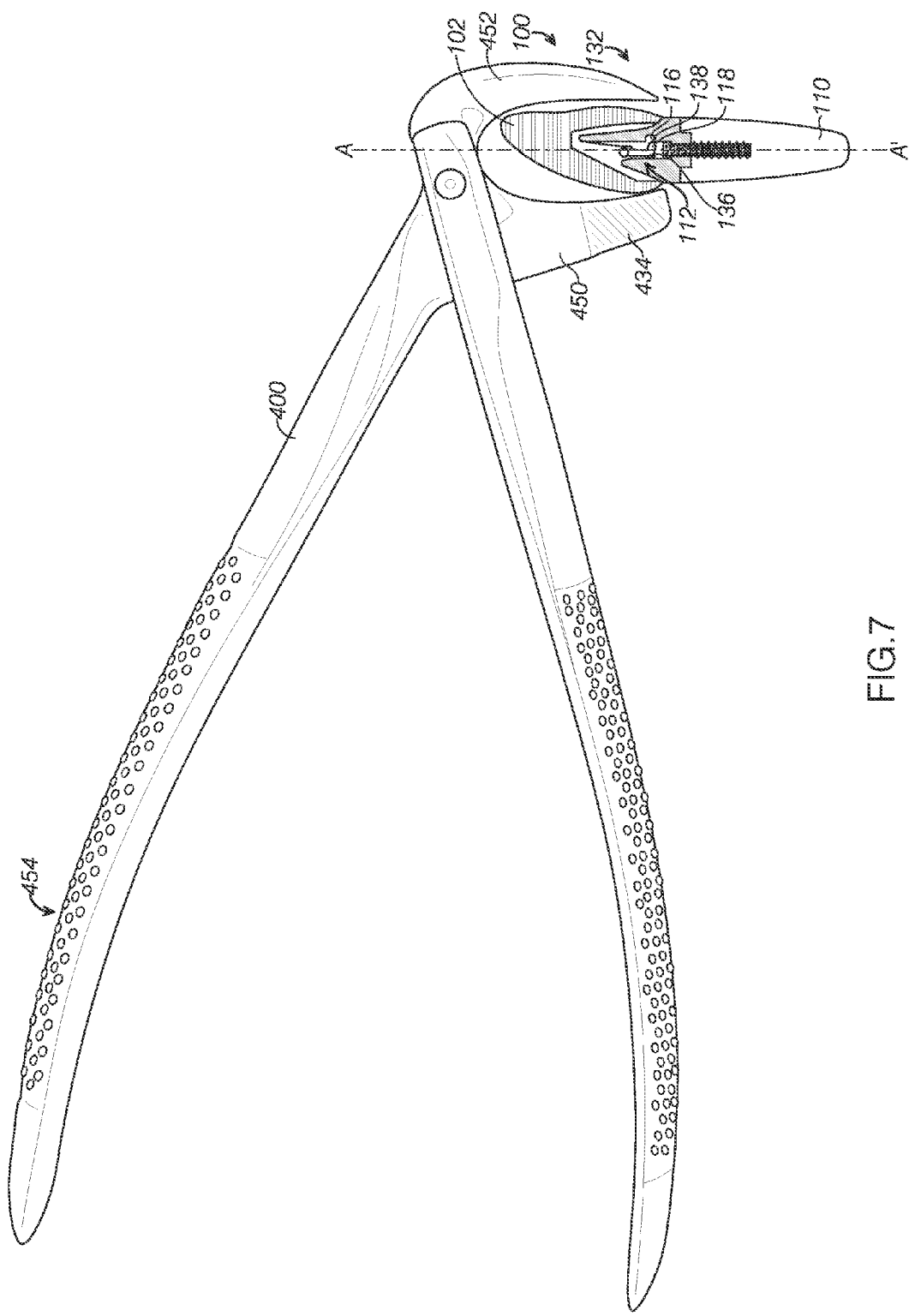
FIG. 7 is a cross-sectional view of the first example dental prosthesis attachment mechanism of FIG. 1 in an unlocked configuration in combination with magnetic dental forceps.

FIG. 7 shows an example forceps device 400 including a magnet 434 being used in combination with attachment system 100. Magnet 434 is located at an end of a prosthesis grasping arm 450, which is proximal to first end 136 of moveable member 116. An opposing prosthesis grasping arm 452 does not include a magnet and is proximal to second end 138 of moveable member 116. Handles 45 can be operated by a dentist or practitioner to grasp prosthesis body 102 and move magnet 434 toward and away from the prosthesis body.

In the orientation shown in FIG. 7, movement of the magnet toward the prosthesis body moves the locking mechanism into the unlocked position, while movement of the magnet away from the prosthesis body moves the locking mechanism into the locked position. During attachment and detachment (i.e., vertical movement along axis A-A'), the forceps grasp the prosthesis body and the locking mechanism is in the unlocked position. After attachment, the forceps release the prosthesis body and the locking mechanism is moved into the locked position. Use of forceps 400 allows easy manipulation of the prosthesis body and operation of the locking mechanism. It will be appreciated that the forceps depicted in FIG. 7 can be used in combination with any of attachment systems 100, 200, and 300.

In summary, the presently described dental prostheses attachment systems have many advantages over known attachment systems. In a first example, less time is required for placement of prostheses when using the presently described attachment systems as compared to conventional techniques. In a second example, the presently described attachment systems are easier, faster, and allow more predictable removal of implant prostheses without damage to the implant prosthesis or implant body when maintenance procedures requiring removal of the prosthesis are needed. In a third example, the presently described attachment systems facilitate better and faster temporary crown construction. In a fourth example, less expensive prosthetics can be achieved with the presently described attachment systems, by the use of prefabricated interchangeable machined parts and less laboratory custom created parts.

In even another example, using the presently described attachment systems, excess sub-gingival cement inadvertently left during the attachment and/or detachment procedures is limited. Cement inadvertently left under the gingiva when cementing dental implant prostheses has been a well-documented source of bone loss around dental implants. With some uses of the presently described attachment systems, no cement will be required and/or used. In certain designs of this device, however, cement may be used to bind the crown or prosthesis to the abutment and/or to the abutment cover. By magnetically releasing the prosthesis post cementation, any excess cement may be easily removed and the prosthesis may then be replaced into correct position using the locking mechanism. In these situations, the cement may be used in the lab or in the oral cavity, as indicated by the clinical situation.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A dental implant system for releasable attachment of a dental prosthesis, comprising:
    an implant body;
    a prosthesis body;
    an abutment body having a locking device, the locking device being at least
        a magnetically attractable member having a first end and a second opposing end, the magnetically attractable member being moveable between a locked position and an unlocked position,
        a spring coupled to the first end, and
        a void configured to receive the second opposing end, the magnetically attractable member being at least partially disposed within the void in the locked position, the magnetically attractable member being free of the void in the unlocked position; and
    a magnetic dental prosthesis removal device configured to be held proximal to the first end to move the magnetically attractable member into the unlocked position, the magnetic dental prosthesis device being a pair of forceps having at least one magnetic arm.

2. The dental implant system of claim 1, wherein the magnetically attractable member is horizontally arranged relative to a vertical axis of the implant body and the prosthesis body.

3. The dental implant system of claim 1, wherein, in the locked position, the magnetically attractable member is configured to resist vertical movement of the prosthesis body away from the implant body, and
    wherein, in the unlocked position, the magnetically attractable member is configured to allow vertical movement of the prosthesis body away from the implant body.

4. The dental implant system of claim 1, wherein the spring biases the magnetically attractable member toward the locked position.

5. The dental implant system of claim 1, wherein the magnetic dental prosthesis device is an electromagnetic device.

6. The dental implant system of claim 1, further comprising a hinge member fixedly attached to the first end of the magnetically attractable member and pivotably attached to a cover for the abutment body, the magnetically attractable member being pivotable between the unlocked position and the locked position.

7. The dental implant system of claim 1, wherein the abutment body further comprises an abutment cover and an abutment main body, an abutment screw configured to threadably attach the abutment main body to the implant body, the prosthesis body fixedly attached to the abutment cover and the spring and the magnetically attractable member being disposed within the abutment cover and the void being disposed within the abutment main body.

8. The dental implant system of claim 7, wherein the magnetically attractable member is configured to releasably attach the prosthetic body and the abutment cover to the abutment body.

9. A dental implant system for attachment of a dental prosthesis, comprising:
    an implant body;
    a prosthesis body;
    an abutment body having a locking mechanism, the locking mechanism being at least
        a horizontal member having a first end and a second opposing end, the horizontal member being moveable from an unlocked position to a locked position, the horizontal member being horizontally arranged relative to a vertical axis of the implant body and the prosthesis body,
        a spring coupled to the first end, the spring being configured to bias the horizontal member toward the locked position, and
        a void configured to receive the second opposing end, the horizontal member being at least partially disposed within the void in the locked position; and
        a hinge member fixedly attached to the first end of the horizontal member and pivotably attached to a cover for the abutment body, the horizontal member being pivotable from the unlocked position to the locked position.

10. The dental implant system of claim 9, wherein the horizontal member is magnetically attractable member, the magnetically attractable member being moveable between the locked position and an unlocked position, the magnetically attractable member being free of the void in the unlocked position, and
    wherein the dental prosthesis is releasably attachable to the abutment body.

11. The dental implant system of claim 9, wherein the abutment body further comprises an abutment cover and an abutment main body, an abutment screw configured to threadably attach the abutment main body to the implant body, the prosthesis body fixedly attached to the abutment cover, the spring and the horizontal member being disposed within the abutment cover and the void being disposed within the abutment main body, and
    wherein the horizontal member is configured to attach the prosthetic body and the abutment cover to the abutment body.

12. A dental implant system for releasable attachment of a dental prosthesis, comprising:
    an implant body;
    a prosthesis body;
    an abutment body having a locking device, the locking device being at least
    a magnetically attractable member having a first end and a second opposing end, the magnetically attractable member being moveable between a locked position and an unlocked position,
    a spring coupled to the first end, and
    a void configured to receive the second opposing end, the magnetically attractable member being at least partially disposed within the void in the locked position, the magnetically attractable member being free of the void in the unlocked position; and
    a hinge member fixedly attached to the first end of the magnetically attractable member and pivotably attached to a cover for the abutment body, the magnetically attractable member being pivotable between the unlocked position and the locked position.

* * * * *